(12) United States Patent
Landoz

(10) Patent No.: US 6,464,497 B2
(45) Date of Patent: Oct. 15, 2002

(54) PACKAGING BOX FOR USE WITH ENDODONTIC INSTRUMENTS

(75) Inventor: Audrey Landoz, Besançon (FR)

(73) Assignee: Micro Mega, S.A., Besançon (FR)

( * ) Notice: Subject to any disclaimer, the term of this patent is extended or adjusted under 35 U.S.C. 154(b) by 0 days.

(21) Appl. No.: 09/826,546

(22) Filed: Apr. 5, 2001

(65) Prior Publication Data

US 2001/0038995 A1 Nov. 8, 2001

(30) Foreign Application Priority Data

Apr. 7, 2000 (FR) .............................. 00 04447

(51) Int. Cl.⁷ .............................................. A61G 15/00
(52) U.S. Cl. ....................................... 433/77; 206/369
(58) Field of Search .......................... 433/102, 77, 75, 433/72; 206/369, 379, 63.5, 368

(56) References Cited

U.S. PATENT DOCUMENTS 5,525,314 A * 6/1996 Hurson ....................... 422/300
5,984,122 A * 11/1999 Barker et al. ............... 215/230
6,328,565 B1 * 12/2001 Rose .............................. 433/77

* cited by examiner

Primary Examiner—Nicholas D. Lucchesi
Assistant Examiner—Melba Bumgarner
(74) Attorney, Agent, or Firm—Gary M. Cohen

(57) ABSTRACT

A container for packaging a plurality of endodontic instruments, and for laying out the endodontic instruments to indicate the preferred sequential use of the instruments by a practitioner, includes a case having a bottom, and a lid for enclosing the bottom of the container. The bottom includes a tray for receiving the endodontic instruments and a plurality of sequence markings which illustrate (for example, by color) progressive operating procedures for using sequences of the endodontic instruments. The lid is removed by the practitioner at the start of a treatment, and includes at least one counter which can be used to indicate the number of times a particular sequence of endodontic instruments has been used.

8 Claims, 1 Drawing Sheet

PACKAGING BOX FOR USE WITH ENDODONTIC INSTRUMENTS

BACKGROUND OF THE INVENTION

The present invention relates to containers for the packaging of endodontic instruments which promote use of the endodontic instruments contained in the package.

In carrying out endodontic treatments, a practitioner will generally use a series of instruments having progressive diameters and/or cone angles to bore out the root canals of the teeth being treated.

To assist the practitioner, a variety of containers for holding endodontic instruments of differing configurations have been developed. In some of these containers, the instruments are laid out on a tray, and the operating procedures suggested for the treatment to be performed are depicted diagrammatically on the tray so that the practitioner can use the instruments in their proper sequence according to a chosen diagram.

To differentiate the endodontic instruments by their diameter, the handles of the instruments are often given a color which corresponds to a particular diameter. For example, the color yellow can be used to designate a number 20 instrument, the color red can be used to designate a number 25 instrument and the color blue can be used to designate a number 30 instrument.

For reasons of asepsis, it is absolutely essential for the instruments to be sterilized, between patients, in cases where the instruments are to be re-used. It is also particularly helpful for the practitioner to know how many times a particular instrument has been used. For example, an instrument which may have already experienced a certain amount of fatigue (resulting from prior uses) can in this way be discarded before running the risk of breakage occurring during treatment. However, because of their size, it is not possible for the instruments to be directly marked with information suitable for implementing such a counting procedure.

It has become increasingly important to provide an effective solution to this problem.

SUMMARY OF THE INVENTION

The present invention constitutes an improvement to containers for the packaging of endodontic instruments, and is particularly well suited to containers in which the various endodontic instruments are laid out with a view to their sequential use by the practitioner.

Generally, this is accomplished by providing a tray which sets out, and diagrammatically illustrates the progressive operating procedures recommended for the endodontic treatment being undertaken. The tray is arranged in a case comprised of a bottom and a lid. The lid is removable from the case, by the practitioner, at the start of each intervention to gain access to the endodontic instruments which are to be used to perform the planned endodontic treatment.

In accordance with the present invention, the case for packaging the endodontic instruments receives the instruments so that the series of endodontic instruments provided in the package are laid out to promote their sequential use by the practitioner. To this end, the series of endodontic instruments are placed on a tray which can also operate to indicate the progressive operating procedures suggested for using the series of instruments. This is preferably accomplished by color-coding the various treatment sequences, although indicia other than color may be used for similar purposes, if desired.

For purposes of color-coding the treatment sequences, a tray comprising at least one treatment sequence is identified by a color, and is arranged in a case comprising a bottom and a lid. The lid of the case is removed by the practitioner at the start of each intervention,.and is further equipped with at least one counter capable of indicating the number of times a sequence has been performed. This, in turn, provides a count of the number of times that a given endodontic instrument has been used.

As an example, for a case containing a series of endodontic instruments arranged in three sequences, with a different color for each of the sequences, three counters are provided on the lid. Each of the counters is then preferably identified by the same color as the corresponding sequence.

As an alternative, the package can be provided with three cases, each of which contains a tray corresponding to a single sequence. The lid for the package would then be provided with a single counter, marked with the color of the corresponding sequence.

Any of a variety of counters can be used to establish any of a variety of desired counts. For example, a count can be made from 0 (for a new sequence), up to a number that corresponds to the manufacturer's recommended maximum number of times that a given instrument should be used.

The counters can be produced in a variety of different ways. For example, rotary devices can be used, and are preferably equipped with detent (clicker) systems which can provide a tactile feel of the position assumed by the counter. The counters can also be produced in the form of linear sliders.

The present invention will be better understood with reference to the detailed description which is provided below, together with the following drawings.

DETAILED DESCRIPTION OF THE INVENTION

Figure 1:
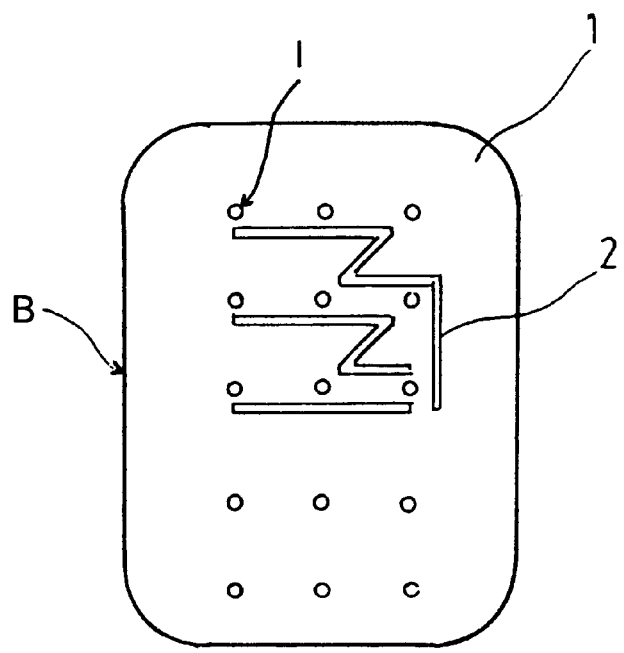
FIG. 1 is a plan view of a tray containing a series of endodontic instruments.
Figure 2:
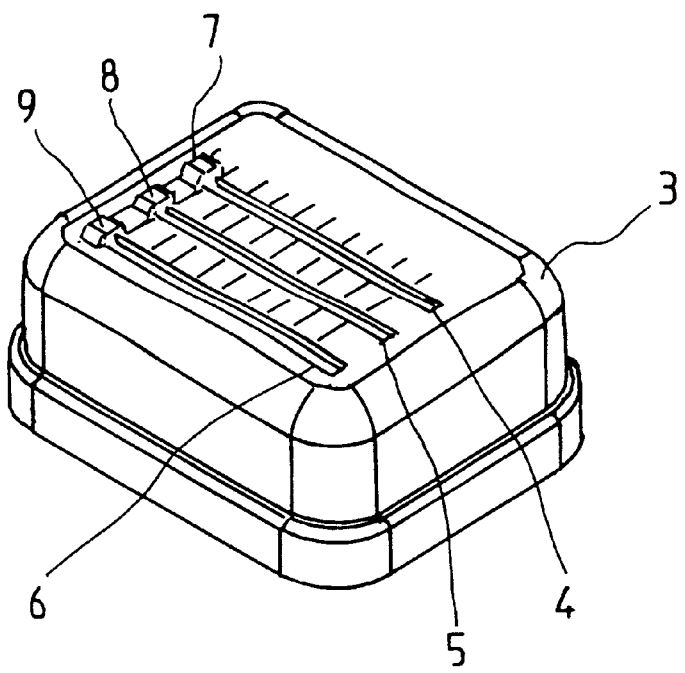
FIG. 2 is an isometric view of a lid for the container of the present invention, in an embodiment which provides three sequences for the instruments provided in the tray.

Known containers for packaging endodontic instruments are generally formed as a case which includes a bottom, and a lid for enclosing the bottom of the container. The bottom (B) of the container includes a tray, such as the tray (1) shown in FIG. 1, for receiving a plurality of endodontic instruments (I). Each of the plurality of endodontic instruments is generally comprised of a handle portion, for use in holding the instrument, and a flexible boring tool extending from the handle, for performing the boring procedure which is desired. As shown in FIG. 1, each of the endodontic instruments (I) is positioned at a right angle to the main plane of the tray (1).

To assist the practitioner, the several endodontic instruments positioned in the tray (1) are arranged in order, primarily in terms of their size and preferably according to their diameter and/or cone angle. As an example, a known instrument sequence can include cone angles of 6%, 4% and 2%, provided for diameters of 0.2 mm (Size 20), 0.25 mm (Size 25) and 0.3 mm (Size 30), respectively. Instruments of an identical diameter (in each series) are identified by a specific (and different) color, which is preferably applied to the handle of each instrument.

The progressive reaming operations which are suggested for a given procedure are depicted diagrammatically, for example, as the sequence markings (2) which are shown on the tray (1).

In accordance with the present invention, the lid (3) is provided with a series of slots (4, 5, 6). Generally, there will be as many slots (4, 5, 6) on the lid (3) as there are colors for marking the handles of the instruments, as previously described. Each of the slots (4, 5, 6) includes a slider (7, 8, 9), which slides in each slot past a series of graduations (e.g., from 0 to 10) provided on each slot. When a selected procedure is to be performed, the slider associated with the color of the selected sequence (2) is advanced to the next graduation. In this way, the number of times that each series of instruments has been used can be seen at a glance, by referring to the graduation which is then adjacent to the slider of a given slot, making it possible to determine when instruments received in the tray (1) are to be discarded.

It will be understood that various changes in the details, materials and arrangement of parts which have been herein described and illustrated in order to explain the nature of this invention may be made by those skilled in the art within the principle and scope of the invention as expressed in the following claims. For example, the configuration of the outer container for the instruments which is selected for illustration in the drawings is only one of a variety of container structures which can be fitted with the counters of the present invention. Although the use of linear sliders is shown in the drawings, for purposes of illustration only, it will be understood that other counting devices can be used to achieve a similar result. For example, any of a variety of rotary devices can be used. The counting devices used are preferably equipped with detent (clicker) systems which can provide a tactile feel of the position assumed by each counter. Although colors have been disclosed for use in identifying the procedure which has been selected, other indicia or markings can be used to achieve a similar result.

What is claimed is:

1. A container for packaging a plurality of endodontic instruments so that the endodontic instruments are laid out for sequential use by a practitioner, comprising a case having a bottom, and a lid for enclosing the bottom, wherein the lid is removable by the practitioner at the start of a treatment, wherein the bottom includes a tray for receiving the endodontic instruments and sequence markings which illustrate progressive operating procedures for using a sequence of the endodontic instruments, and wherein the lid includes at least one counter for indicating a number of times that the sequence of the endodontic instruments has been used.

2. The container of claim 1 wherein the sequence markings are identified by a color.

3. The container of claim 2 which includes three counters, each marked with a color corresponding to a color which identifies the sequence of the endodontic instruments.

4. The container of claim 3 wherein each of the counters includes markings for developing counts from 0, for a new sequence, to a number corresponding to a recommended maximum number of times an instrument is to be used.

5. The container of claim 1 wherein the at least one counter includes markings for developing counts from 0, for a new sequence, to a number corresponding to a recommended maximum number of times an instrument is to be used.

6. The container of claim 1 wherein the at least one counter is a linear slider received within a slot so that the slider is capable of movement along the slot.

7. The container of claim 6 wherein the slot is mated with a plurality of markings for counting the number of times the sequence of the endodontic instruments has been used.

8. The container of claim 6 wherein the at least one counter includes a detent system for providing a tactile feel of a position assumed by the slider.

* * * * *